United States Patent [19]

Goodnoe

[11] Patent Number: 4,974,584

[45] Date of Patent: Dec. 4, 1990

[54] EMERGENCY AIR SUPPLY ASSEMBLY FOR TRAPPED FIRE FIGHTERS

[76] Inventor: Ronald R. Goodnoe, 10618 Petrieville Hwy., Eaton Rapids, Mich. 48827

[21] Appl. No.: 496,140

[22] Filed: Mar. 19, 1990

Related U.S. Application Data

[63] Continuation of Ser. No. 367,846, Jun. 19, 1989, abandoned.

[51] Int. Cl.[5] ........................ A61M 15/00; A62O 9/04

[52] U.S. Cl. ........................... 128/202.13; 128/202.27; 239/270; 239/289

[58] Field of Search ....................... 128/202.13, 201.29, 128/204.18, 206.28, 207.12, 205.24, 205.25, 200.28, 202.27; 239/270, 289

[56] References Cited

U.S. PATENT DOCUMENTS

| | | | |
|---|---|---|---|
| 667,840 | 2/1901 | Guthrie | 128/202.13 |
| 752,266 | 2/1904 | Thompson | 128/202.13 |
| 811,021 | 1/1906 | Wood . | |
| 958,427 | 5/1910 | Panian | 128/202.13 |
| 996,739 | 7/1911 | Vinton . | |
| 1,040,311 | 10/1912 | Halloran | 128/202.13 |
| 1,084,958 | 1/1914 | Panian . | |
| 1,491,752 | 1/1970 | Cowley . | |
| 1,630,209 | 5/1927 | Olgard | 128/205.25 |
| 1,974,828 | 9/1934 | Markut | 128/200.28 |
| 2,515,578 | 7/1950 | Wilson et al. | 128/202.13 |
| 3,038,472 | 6/1962 | Gaylord | 128/202.27 |
| 3,068,865 | 12/1962 | Laszlo | 128/200.28 |
| 3,486,730 | 12/1969 | Potash | 128/202.27 |
| 3,521,529 | 7/1970 | Reynolds . | |
| 4,250,876 | 2/1981 | Kranz . | |
| 4,702,243 | 10/1987 | Smith . | |
| 4,846,167 | 7/1989 | Tibbais | 128/202.27 |

*Primary Examiner*—Eugene H. Eickholt
*Attorney, Agent, or Firm*—Beaman & Beaman

[57] ABSTRACT

The invention is an emergency air supply assembly for delivery of air to trapped fire fighters, the combination comprising:

a fire truck having a water supply outlet with a water shut-off valve and an air connector collar provided for selective operative engagement with the water outlet, the air connector collar having an emergency air connector quick coupler check valve assembly provided therethrough, the air collar adapted for selective operative engagement with the entry end of a fire hose having nozzle at the opposite end thereof; and an air supply provided in association with the fire truck, the emergency air supply adapted for snap engagement with the air connected quick coupled assembly so as to permit delivery of emergency breather air through the fire hose upon selective closure of the water shut-off valve.

14 Claims, 5 Drawing Sheets

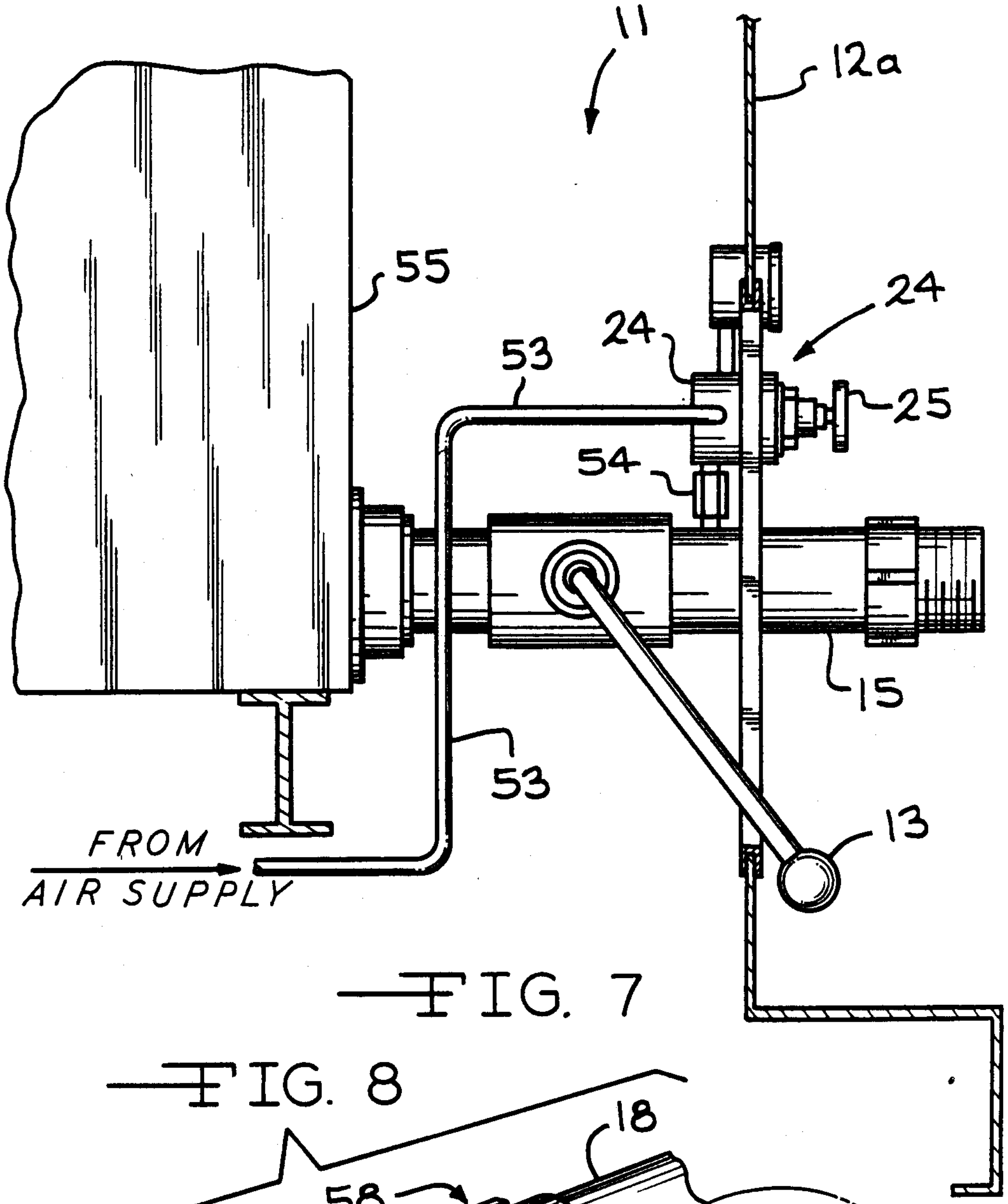
FIG. 7
FIG. 8
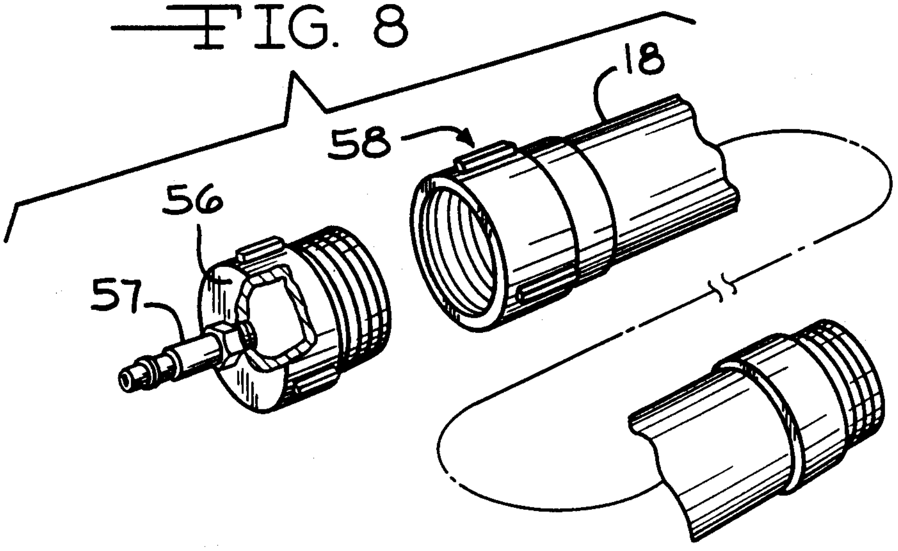

EMERGENCY AIR SUPPLY ASSEMBLY FOR TRAPPED FIRE FIGHTERS

This is a continuation application of Ser. No. 367,846, filed Jun. 19, 1989 and now abandoned.

This invention relates to an emergency air supply assembly for fire fighters which is adapted to provide emergency breathing air through a fire hose to fire fighters and/or rescue teams trapped within a burning structure or a structure filled with potentially explosive and/or toxic gas.

The emergency air supply assembly comprises emergency air snap coupling means provided in association with the fire hose to permit quick coupling of an emergency air supply unit with the entry end of the fire hose for emergency delivery of breathing air to the trapped fire fighters and/or rescue teams. In such an emergency, the portable air supply unit normally carried by the fire fighters becomes exhausted when the fire fighters become trapped. Unless the fire fighters can be rescued immediately, they will die of suffocation. The instant invention enables emergency air to be instantly delivered to the trapped fire fighters by easily and quickly converting the fire hose being used by the fire fighters for normal water delivery to use for emergency air delivery. In operation during such an emergency, the water supply to the fire hose is shut off and the emergency air supply assembly is snap connected to the entry end of the fire hose. The trapped fire fighters place the nozzle end of the fire hose into an emergency air collector member, such as a bag, a boot or even an article of clothing, which traps the emergency air for use by the firemen. The breathing mask tube normally connected to the portable air supply unit (now exhausted) carried by the fire fighters is then inserted into the emergency air collector member so as to provide emergency air to the fire fighters. If several fire fighters in an entire crew are trapped, they can insert their respective breathing mask tubes into the emergency air collector member so as to simultaneously receive emergency breathing air therefrom, thereby saving their collective lives until they are rescued.

It is within the scope of the invention that the trapped fire fighting and/or rescue crews can thus be supplied with emergency air if they are located within a closet, tent, tarpaulin covers or any other type of enclosed space which can act as an emergency air collector member.

Another embodiment of the invention is to provide a fire hose which is selectively provided with an entry end closure cap having an air connector snap engagement member provided therethrough for connection to an independent emergency air supply assembly such as a bank of air tanks or an air compressor. Further, this closure cap embodiment of the invention can enable the firehose to be independently used to deliver emergency air to persons trapped underwater in sunken boats and or in automobiles that have broken through ice or been inadvertently driven into rivers, lakes or water filled ditches. An emergency air supply source is snap connected to the air connector provided in the closure cap provided on the entry end of the fire hose. The firehose is then pulled underwater to the trapped vehicle or boat and the nozzle end is placed into the area in which the persons are trapped so as to supply emergency breathing air to the trapped person or persons. The fire hose can thus be used independently of a fire truck thus permitting the fire truck to continue to be used to deliver water through another fire hose to other areas of the fire.

Nowhere in the structures or methods of the prior known art has there been shown an emergency breathing air supply structure and/or method such as the applicant's structure and/or method whereby a fire hose can be easily and quickly converted from the delivery of water to the delivery of emergency breathing air to trapped fire fighters, rescue teams within structures filled with toxic or explosive gases, or persons trapped in vehicles located under water. Heretofore, persons trapped without a readily available breathing air supply have been suffocated before rescue teams could reach them.

Therefore, a need has existed for an emergency breathing air supply structure and method whereby persons trapped without breathing air can be kept alive and prevented from suffocating until they are rescued and removed from their trapped positions.

It is therefor an object of this invention to provide an emergency breathing air supply structure and method whereby emergency breathing air can be easily and quickly delivered to fire fighters trapped within burning or toxic gas filled structures or to persons trapped in sunken boats, vehicles or other spaces located underwater.

Another object of this invention is to provide an emergency breathing air supply structure and method whereby a standard fire hose can be easily and instantaneously converted from the delivery of water to the delivery of emergency breathing air to persons trapped in burning or toxic filled structures normally carried portable supply of breathing air has been terminated or exhausted.

Another object of this invention is to provide emergency breathing air to persons trapped underwater so as to prevent their suffocation until they can be rescued.

Other objects and advantages found in the construction of the invention will be apparent from a consideration of the following specification in connection with the appended claims and the accompanying drawings.

IN THE DRAWINGS

FIG. 7 is a partial schematic cross-sectional view of a firetruck showing another embodiment of the emergency breathing air supply assembly integrated into the fire truck body and water outlet tube in association with the fire hose attached externally thereto.

FIG. 8 is a partial schematic perspective view showing another embodiment of a firehose provided with an entry end closure cap having an air connector therethrough for selective snap attachment with emergency air supply means.

DESCRIPTION

Figure 1:
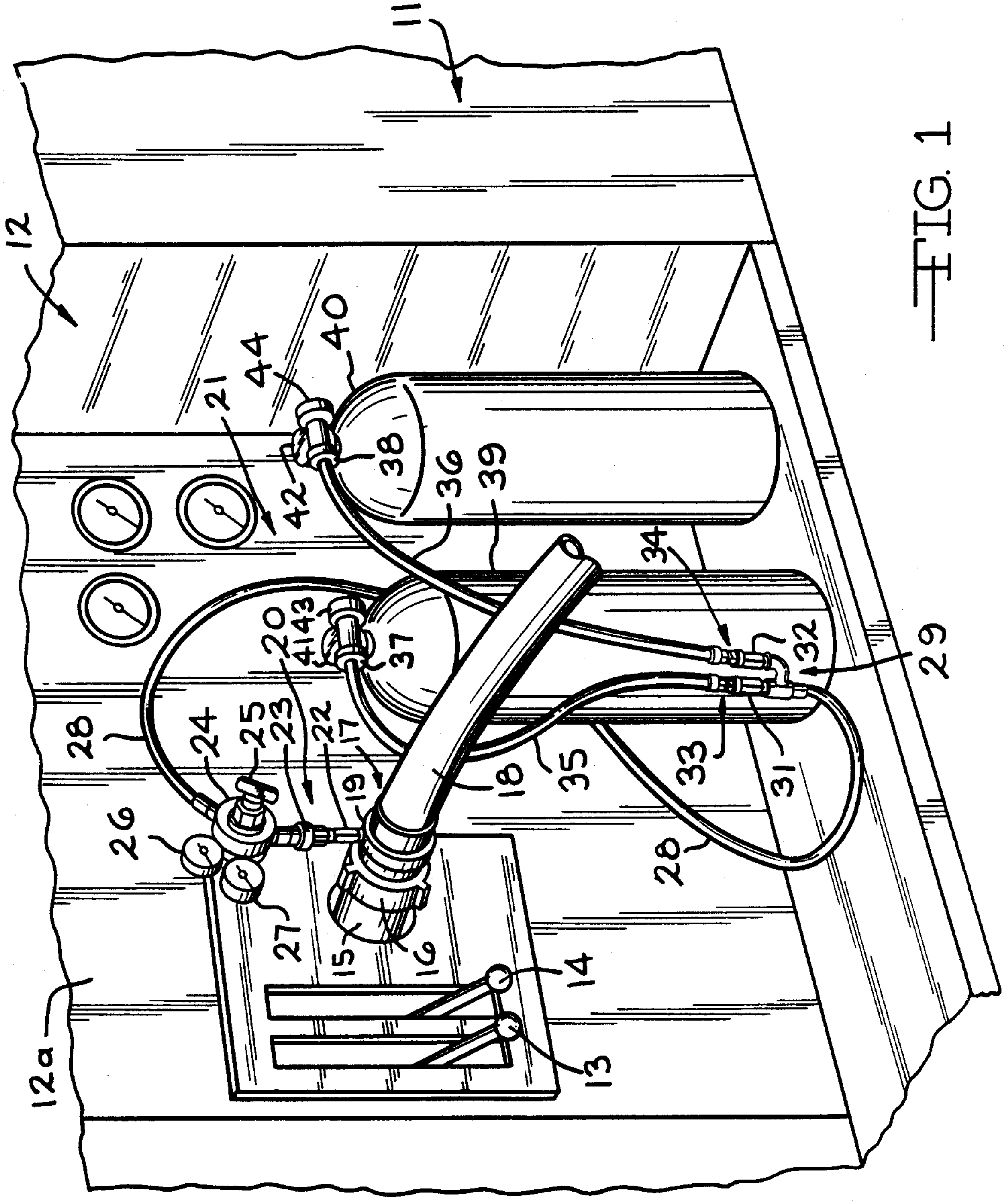
FIG. 1 is a partial perspective view of a portion of a firetruck with a firehose attached thereto and showing the emergency breathing air supply assembly attached thereto.

As shown in FIG. 1, a fire truck 11 is provided with a fire hose control panel area 12. The fire truck is provided with water shut off control levers 13 and 14 which are connected to water supply tanks and associated water pumps (not shown) which are internally provided in the fire truck. A fire truck water outlet 15 is provided for selective threaded engagement by a fire truck water outlet adaptor 16 which engages an air connector collar 19 having an air connector quick coupler assembly 20 provided therethrough and which is connected to the entry end 17 of the fire hose 18. The emergency air connector quick coupler assembly 20 is adapted to deliver emergency breathing air through the air connector collar 19 into the fire hose 18 when it is connected to an emergency breathing air supply assembly 21.

The emergency air quick coupler assembly 20 includes a pressure check valve 22 and air connector quick coupler unit 23. The air connector assembly 20 is connected to a high pressure to low pressure regulator unit 24 having an adjustment control handle 25. The regulator unit 24 is provided with an air supply tank pressure gage 26 and an exit air pressure gage 27. A high pressure air supply hose 28 supplies air to the regulator 24 from the air supply assembly 21.

Figure 2:
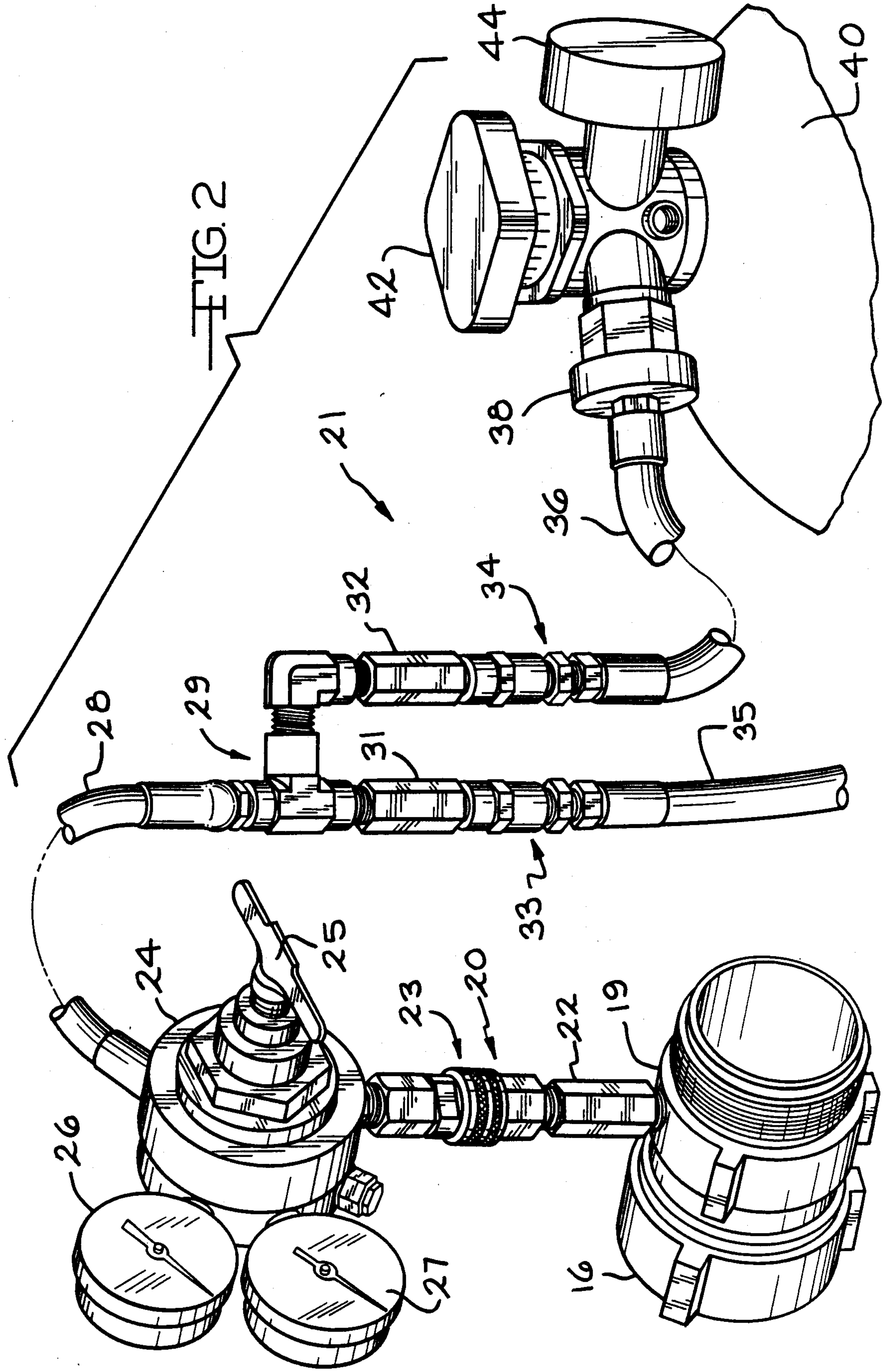
FIG. 2 is a schematic perspective view showing the emergency breathing air supply assembly and associated control valves.

As shown in greater detail in FIG. 2, the high pressure air supply hose 28 is connected to a high pressure tee connector 29 provided for selective connection to one or more air supply tanks 39 and 40. The tee connector 29 is provided with minimum 2500 pound high pressure check valves 31 and 32 which are in turn connected by couplers 33 and 34, respectively, to high pressure tank supply hoses 35 and 36, respectively. The opposite ends of the hoses 35 and 36 are connected to air tank coupler 37 and 38 provided on air tanks 39 and 40, respectively. Each air tank, 39 and 40 is provided with air pressure gages 41 and 42 and shut off valves 43 and 44 respectively.

In an emergency involving fire fighters or other trapped persons needing emergency air, the appropriate fire truck water shut off control lever 13 or 14 is lifted to shut off delivery of water to the fire hose 18.

The emergency breathing air supply assembly 21 as shown generally in FIG. 1 and more specifically in FIG. 2 is uniquely designed to provide a continuous supply of breathing air into the fire hose 18 from the air tanks 39 and 40 because of the critically positioned air check valves 31 and 32 provided between the inlets to the tee 29 and tank supply hoses 35 and 36 connected to the air supply tanks 39 and 40, respectively. In use, the shut off valve 43 is opened on tank 39 and air flows therefrom into the hose 35 through the check valve 31 into hose 28 to the regulator 24 and thence through the emergency air connector quick coupler assembly 20 into the fire hose 18 for delivery of the emergency breathing air to the trapped persons. As tank 39 nears empty, the shut off valve 44 on tank 40 is opened and the air supply continues to flow without interruption through the tee 29 into the fire hose 18 as described above. The check valve 31 prevents the air from tank 40 from entering the tube 35 and the near empty tank 39. The check valve 31 also permits the near empty tank 39 to be disconnected from tube 35 so as to be replaced by a full tank 39 without interruption of the flow of air from tank 40 to the trapped fire fighters. The same procedure is followed when tank 40 becomes nearly empty. Thus, the shut off valve 43 on the now full new replacement tank 39 is opened so as to maintain a continuous flow of air to the fire hose 18. The check valve 32 prevents air from tank 39 from flowing back into the hose 36 to the now nearly empty tank 40 and permits replacement of tank 40 without any interruption of the air flow from the now full tank 39 to the trapped persons. This process is repeated as required. It is within the scope of the invention to increase the bank of air supply tanks with similarly placed check valves in association therewith so that a continuous flow of emergency breathing air is maintained at all times during the emergency.

Figure 3:
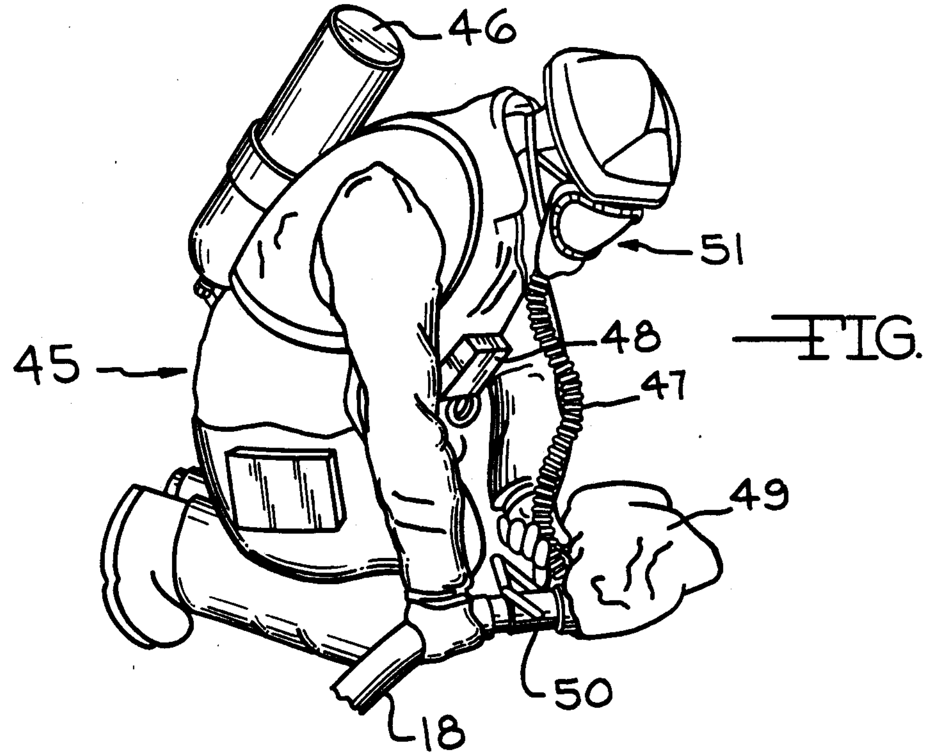
FIG. 3 is a perspective view of a fire fighter receiving emergency breathing air from an air collector bag supplied by the emergency air from the nozzle end of the fire hose.
Figure 4:
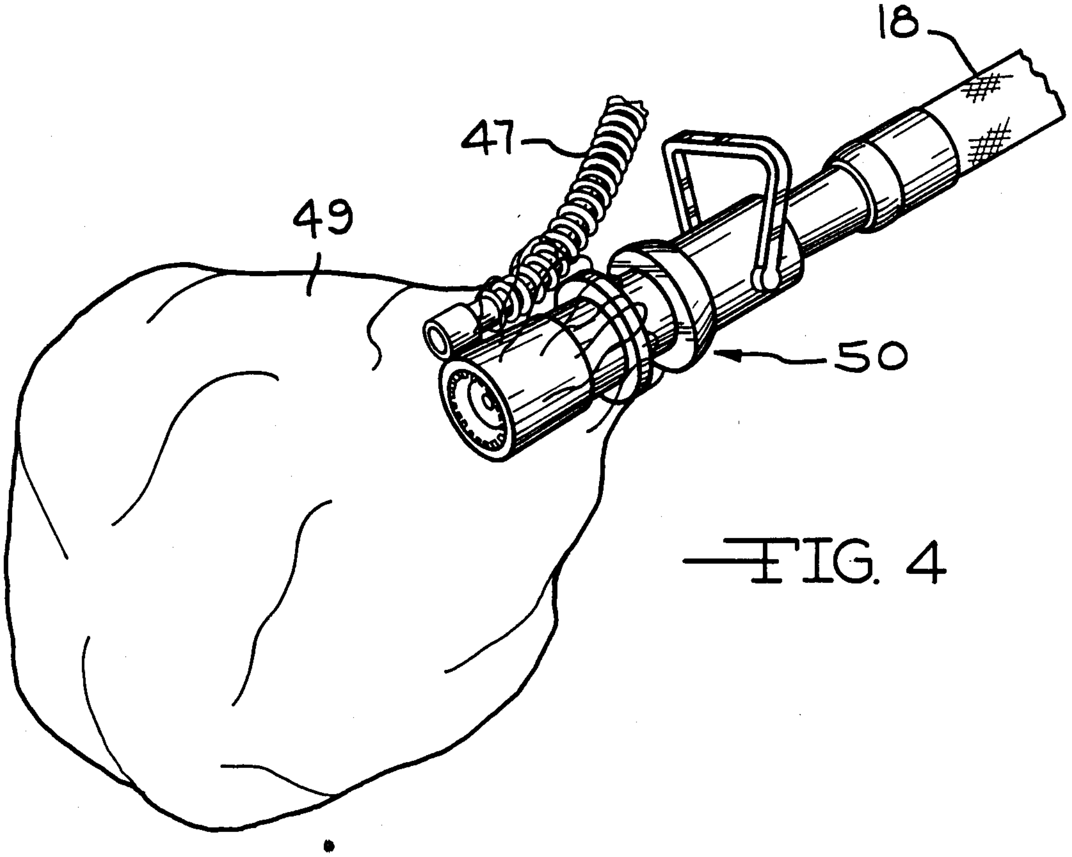
FIG. 4 is a partial enlarged schematic perspective view of the emergency air collector member showing the nozzle end of the emergency air delivery fire hose and the fire fighter's fire mask air tube positioned therein.

As shown in FIG. 3, the trapped fire fighter 45 whose portable air supply tank 46 has run out of air quickly disconnects his breathing tube 47 from portable air tank air supply regulator unit 48 and places it into an air collector bag 49. The fire fighter 45 has also inserted the nozzle end 50 of the fire hose 18 into the collector bag 49 so that the emergency air passes thereinto. This is shown in greater detail in FIG. 4.

In this manner the fire fighter is able to breathe emergency air from the collector bag 49 through the breathing tube 47 into his mask 51. Thus, the fire fighter does not suffocate while waiting to be rescued.

Figure 5:
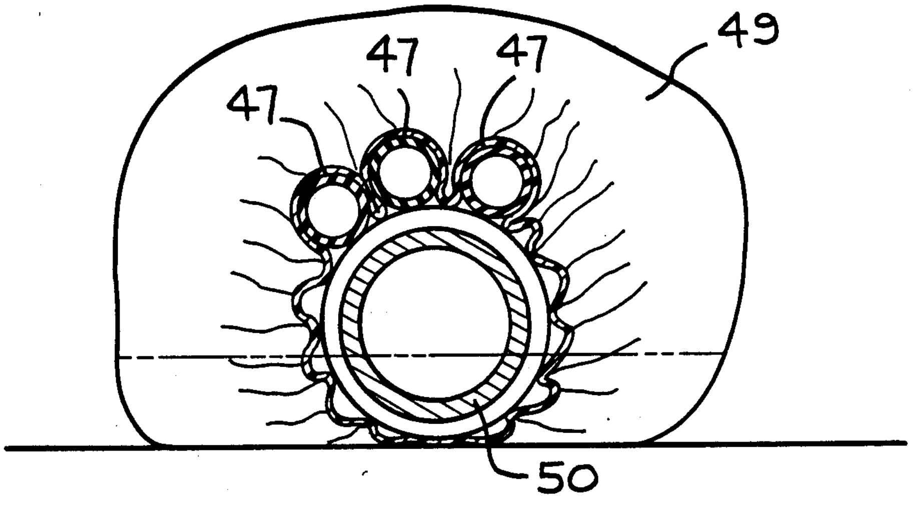
FIG. 5 is a schematic end sectional view showing the air collector bag with the fire hose nozzle and three fire fighter air tubes receiving air therefrom.

As shown in FIG. 5, several members of a trapped crew can simultaneously insert their respective breathing tube 47 into the air collector member 49 so as to save their lives.

Figure 6:
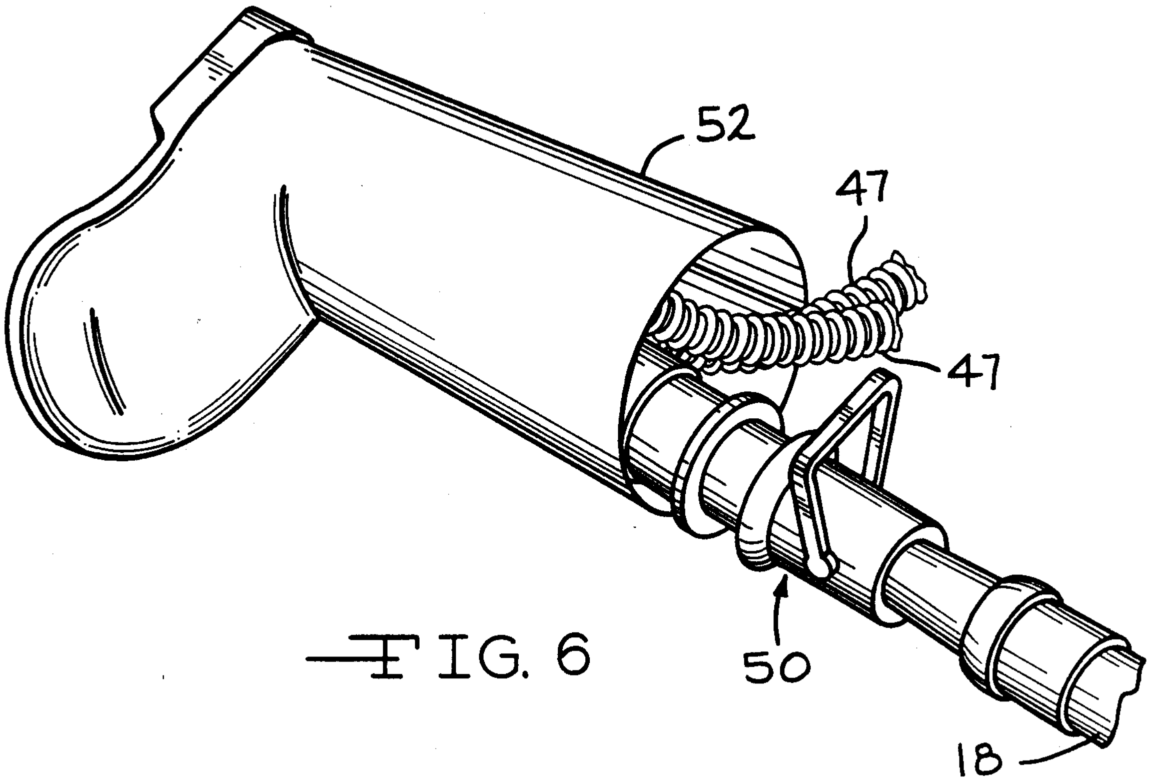
FIG. 6 is a schematic view showing a fire fighter's boot utilized as an emergency air collector member.

As shown in FIG. 6, it is within the scope of the invention to selectively use a boot 52 as an emergency air collector member. The air collector member can also be a coat pocket, the person's shirt, a closet or the confines of a sunken automobile if the person is trapped therein.

Another embodiment of the invention is shown in FIG. 7 wherein the air regulator 24 and associated controls and gages are incorporated into the fire truck control panel wall 12*a* and a remote air supply assembly or air compressor (not shown) is utilized to supply emergency air through the air supply tube 53 the regulator 24. An air connector check valve 54 transmits the air into the water outlet tube 15 and hence into the fire hose 18 (not shown). Thus in an emergency, the water lever 13 is lifted to shut off the water supply from the water tank 55 and associated water pump (not shown). Then the air regulator 24 and emergency air means are actuated to supply emergency breathing air into the fire hose 18 as previously described. This could be mounted elsewhere on the truck or constitute a multiple bank of air tanks or an air compressor.

Another embodiment of the invention is shown in FIG. 8 whereby a fire hose closure cap 56 is provided with an air connector snap engagement member 57 mounted through the end wall thereof. It is within the scope of the invention to provide the air connector member 57 through the side of the closure cap 56 as desired. The cap 56 is selectively mounted at the entry end 58 of the fire hose 18 so as to effect closure thereof. Thus mounted, the closure cap 56 permits emergency air to be introduced therethrough by connection thereto of air supply means of any type, i.e. air tanks, compressors and the like to the air connector 57 which delivers the air through the closure cap 56 into the fire hose 18. As previously described, the emergency breathing air is then delivered to the trapped persons so as to keep them alive. The closure cap embodiment of the invention permits the fire hose 18 to be disconnected from the fire truck for emergency air supply use permitting the fire truck to use another hose to deliver water as needed. It is also within the scope of the invention to modify the air supply means for direct mating engagement with the fire hose 18 so as to deliver breathing air thereinto without the need for closure caps and the like.

In summary, an emergency air supply assembly is provided for delivery of emergency breathing air to trapped fire fighters. dated water pump (not shown). Then the air regulator 24 and emergency air means are actuated to supply emergency breathing air into the fire hose 18 as previously described. This could be mounted elsewhere on the truck or constitute a multiple bank of air tanks or an air compressor.

Another embodiment of the invention is shown in FIG. 8 whereby a fire hose closure cap 56 is provided with an air connector snap engagement member 57 mounted through the end wall thereof. It is within the scope of the invention to provide the air connector member 57 through the side of the closure cap 56 as desired. The cap 56 is selectively mounted at the entry end 58 of the fire hose 18 so as to effect closure thereof. Thus mounted, the closure cap 56 permits emergency air to be introduced therethrough by connection thereto of air supply means of any type, i.e. air tanks, compressors and the like to the air connector 57 which delivers the air through the closure cap 56 into the fire hose 18. As previously described, the emergency breathing air is then delivered to the trapped persons so as to keep them alive. The closure cap embodiment of the invention permits the fire hose 18 to be disconnected from the fire truck for emergency air supply use permitting the fire truck to use another hose to deliver water as needed. It is also within the scope of the invention to modify the air supply means for direct mating engagement with the fire hose 18 so as to deliver breathing air thereinto without the need for closure caps and the like.

In summary, an emergency air supply assembly is provided for delivery of emergency breathing air to trapped fire fighters. A fire truck is provided having a water supply outlet. The water supply outlet has a water shut-off valve in association therewith. Air connector collar means is provided for selective operative engagement with the water outlet. The air connector collar means is provided with an emergency air connector quick coupler check valve assembly provided therethrough. The air collar means is adapted for selective operative engagement with the entry end of a fire hose having nozzle at the opposite end thereof. Emergency air supply means are provided in association with the fire truck. The emergency air supply means are adapted for snap engagement with the air connector quick coupler assembly so as to permit delivery of emergency breathing air through the fire hose to trapped fire fighters positioned proximate to the nozzle end of the fire hose upon selective closure of the water shut off valve. The emergency air connector quick coupler assembly includes a pressure check valve and an air connector quick coupler unit for selective operative engagement with the air connector collar means. The emergency air supply means include a high pressure to low pressure air regulator unit for selective engagement with the emergency air connector quick coupler assembly. The emergency air supply means include a regulator high pressure air supply hose operatively connected at one end thereof to the air regulator. The emergency air supply means include a high pressure tee connector operatively connected at the outlet end thereof to the regulator high pressure air supply hose. The high pressure tee connector is provided with a pair of inlet ends. Each of the inlet ends is provided with an inlet high pressure check valve. Each of the inlet high pressure check valves are operatively connected to their own separate air supply tank, respectively. Each of the air supply tanks are provided with a shut off valve. The high pressure check valves cooperate with selective actuation of the air tank shut off valves to provide a continuous supply of emergency air. An air collector member is provided for selective engagement with the fire hose nozzle. The air collector member is adapted to collect emergency air received through the fire hose nozzle. The air collector member is adapted to simultaneously selectively receive a fire fighter's breathing tube therein for use of emergency air by the trapped fire fighter.

Another embodiment of the emergency air supply assembly for trapped fire fighters comprises a fire truck having a control panel provided with water supply outlet. The water supply outlet is provided with a water shut-off valve in association therewith. A high pressure to low pressure air regulator unit is provided in the control panel. The air regulator is provided with a remote air supply inlet tube in operative engagement therewith. The air regulator is provided with an air supply check valve outlet tube in operative engagement with the water supply outlet. The air regulator, upon selective closure of the water shut off valve, is adapted to selectively supply emergency breathing air through the water supply outlet into a fire hose operatively connected thereto for subsequent delivery to trapped fire fighters.

Yet another embodiment of the emergency air supply assembly for delivery of emergency air to trapped persons comprises a fire hose having an entry end. The fire hose has a nozzle end opposite the entry end. An entry end fire hose closure cap is provided for selective operative engagement with the entry end of the fire hose. The closure cap is provided with a snap-engagement air delivery connector therethrough. The air connector is adapted for selective snap engagement to an emergency air supply source so as to deliver emergency air through the closure into the fire hose for delivery of emergency air to trapped persons positioned proximate to the nozzle end of the fire hose.

Various other modifications of the invention may be made without departing from the principle thereof. Each of the modifications is to be considered as included in the hereinafter appended claims unless these claims by their language expressly provide otherwise.

We claim:

1. In an emergency air supply assembly for delivery of emergency breathing air to trapped fire fighters, the combination comprising:

a fire truck having a water supply outlet, said water supply outlet having a water shut-off valve in association therewith.

an air connector collar means provided for selective operative engagement with said water outlet, said air connector collar means having an emergency air connector quick coupler check valve assembly provided therethrough, said air collar means adapted for selective operative engagement with the entry end of a fire hose having nozzle at the opposite end thereof; and emergency air supply means provided in association with said fire truck, said emergency air supply means adapted for snap engagement with said air connector quick coupler assembly so as to permit delivery of emergency breathing air through said fire hose to trapped fire fighters upon selective closure of said water shut-off valve.

2. In the emergency air supply assembly of claim 1 wherein said emergency air connector quick coupler assembly includes a pressure check valve and air connector quick coupler unit for selective operative engagement with said air connector collar means.

3. In the emergency air supply assembly of claim 1 wherein said emergency air supply means include a high pressure to low pressure air regulator unit for selective engagement with said emergency air connector quick coupler assembly.

4. In the emergency air supply assembly of claim 3 wherein said emergency air supply means include a regulator high pressure air supply hose operatively connected at one end thereof to said air regulator.

5. In the emergency air supply assembly of claim 4 wherein said emergency air supply means include a high pressure tee connector operatively connected at the outlet end thereof to said regulator high pressure air supply hose, said high pressure tee connector having a pair of inlet ends, each of said inlet ends provided with an inlet high pressure check valve.

6. In the emergency air supply assembly of claim 5 wherein each of said inlet high pressure check valves are operatively connected to a separate air supply tank, each of said air supply tanks having a shut off valve, said high pressure check valves cooperating with selective actuation of said shut-off valves to provide a continuous supply of emergency air.

7. In the emergency air supply assembly of claim 1 wherein an air collector member is provided for selective engagement with said fire hose nozzle, said air collector member adapted to collect emergency air received through said fire hose, said air collector member adapted to simultaneously selectively receive a fire fighter's breathing tube therein for use by the trapped fire fighter.

8. In an emergency air supply assembly for trapped fire fighters, the combination comprising:

a fire truck having a control panel provided with water supply outlet, said water supply outlet having a water shut-off valve in association therewith;

a high pressure to low pressure air regulator unit provided in said control panel, said air regulator having a remote air supply inlet tube in operative engagement therewith, said air regulator provided with an air supply check valve outlet tube in operative engagement with said water supply outlet, said air regulator upon selective closure of said water shut-off valve adapted to selectively supply emergency breathing air through said water supply outlet into a fire hose operatively connected thereto for subsequent delivery to trapped fire fighters.

9. An emergency air supply assembly for delivery of emergency breathing through a conventional flexible fire hose through which water under pressure is normally ejected having an entry end, a discharge end, and a hose fitting mounted upon the hose entry end, comprising, in combination:

(a) an adapter adapted to be affixed to the hose fitting having an interior in communication with the hose, and (b) a pressurized air supply fitting mounted upon said adapter in communication with said adapter interior whereby pressurized air may be introduced into said air supply fitting and into the fire hose for discharge through the fire hose discharge end.

10. In an emergency air supply as in claim 9, said adapter comprising a closure cap adapted to be sealingly affixed to the hose fitting.

11. In an emergency air supply as in claim 10, the hose fitting and said closure cap each including complementary threads, said cap being connectable by its threads to the threads of the hose fitting.

12. In an emergency air supply as in claim 9, said adapter comprising an annular collar first and second ends, first connection means defined on said collar first end for affixing said collar first end to the hose fitting, and second connection means defined on the collar second end for affixing said collar second end to a water supply outlet.

13. In an emergency air supply as in claim 9, emergency air supply means adapted to communicate with said air supply fitting to supply emergency breathing air to said adapter and to the hose fitting and fire hose.

14. In an emergency air supply as in claim 13, said emergency air supply means including a pressure check valve.

* * * * *